(12) United States Patent
Hök

(10) Patent No.: US 6,843,101 B2
(45) Date of Patent: Jan. 18, 2005

(54) $CO_2$ SENSOR

(76) Inventor: Bertil Hök, Knektgatan 1F, 723 44 Västerås (SE)

( * ) Notice: Subject to any disclaimer, the term of this patent is extended or adjusted under 35 U.S.C. 154(b) by 0 days.

(21) Appl. No.: 10/398,734

(22) PCT Filed: Oct. 8, 2001

(86) PCT No.: PCT/SE01/02175

§ 371 (c)(1),
(2), (4) Date: Aug. 20, 2003

(87) PCT Pub. No.: WO02/31488

PCT Pub. Date: Apr. 18, 2002

(65) Prior Publication Data

US 2004/0050142 A1 Mar. 18, 2004

(51) Int. Cl.[7] .............................................. G01N 29/02
(52) U.S. Cl. ...................... 73/24.01; 73/23.21; 73/24.06
(58) Field of Search ............................. 73/23.21, 24.01, 73/24.06

(56) References Cited

U.S. PATENT DOCUMENTS

| | | | | |
|---|---|---|---|---|
| 4,220,040 A | * | 9/1980 | Noguchi et al. ............ | 73/24.01 |
| 4,280,183 A | * | 7/1981 | Santi ............................ | 702/24 |
| 4,380,167 A | * | 4/1983 | Longini ....................... | 73/24.01 |
| 4,520,654 A | * | 6/1985 | Terhune ....................... | 73/24.01 |
| 5,060,506 A | * | 10/1991 | Douglas ....................... | 73/24.01 |
| 5,285,677 A | * | 2/1994 | Oehler ......................... | 73/24.01 |
| 5,313,820 A | * | 5/1994 | Aylsworth ................... | 73/24.01 |

FOREIGN PATENT DOCUMENTS

| | | | | |
|---|---|---|---|---|
| DE | 3009566 | * | 9/1981 | ................. 73/24.01 |
| EP | 0 174 627 | | 3/1986 | ................. 73/24.01 |
| GB | 727891 | | 4/1955 | ................. 73/24.01 |
| GB | 2203247 | * | 12/1988 | ................. 73/24.01 |
| GB | 2210977 | * | 6/1989 | ................. 73/24.01 |
| GB | 2257255 | | 1/1993 | ................. 73/24.01 |

OTHER PUBLICATIONS

Swedish published application SE 200000108A, Jul. 18, 2001, (abstract and drawing figure only).*

* cited by examiner

*Primary Examiner*—Daniel S. Larkin
(74) *Attorney, Agent, or Firm*—Young & Thompson

(57) ABSTRACT

A sensor for the measurement of carbon dioxide concentration within an air flow being input to a measuring cell (1) connected to at least one electroacoustic element (2, 3) for transmitting and receiving airborne acoustic waves within the measuring cell (1). The output signal of the sensor corresponds to the propagation velocity of these waves and an indirect measure of carbon dioxide concentration, with an automatic offset correction functionality for compensation of undesired offset variations of the signal, caused by temperature or humidity variations. Preferably, an accumulating function for minimizing the influence of the offset variations is included, which for humidity variations may consist of a material with high porosity and surface density of polar molecular groups. Temperature control of the inner sheath (4) is effected by a temperature sensor (11), a resistive heating element (12) in good thermal contact with the inner sheath (4), and a control circuit (13).

9 Claims, 1 Drawing Sheet

CO₂ SENSOR

BACKGROUND OF THE INVENTION

Dry atmospheric air consists of a mixture of nitrogen (78.1% by volume), oxygen (20.9%), inert gases (1.0%), and carbon dioxide (360 ppm, parts per million). The concentration of water vapor is seldom more than a few percent, but exhibits large geographical variations, depending on climate and weather. The $CO_2$ concentration is both locally and globally of a dynamic character. Regardless of large buffer reservoirs of $CO_2$ in the oceans, and in the earth's crust, the balance is determined by the build-up and breaking down of biological material. As a result of the combustion of fossil fuel, the $CO_2$ concentration is increasing by approximately 2 ppm/year. A continuing increase is feared to cause significant climate changes, the so called green house effect. Locally, the outdoor $CO_2$ concentration may rise a few hundred ppm above the mentioned background level, as a result of local biological processes, traffic intensity, industrial exhaust etc.

The indoor $CO_2$ concentration is likewise an indicator of biological activity in relation to the ventilation of the locality with fresh outdoor air. Human expired air contains approximately 4% $CO_2$, which results in fast increase of the indoor $CO_2$ concentration at high person density and low ventilation rate. After entrance of a person in an empty room, an increasing $CO_2$ concentration can be detected already after a few minutes. The concentration continues to rise until it reaches a level determined by the ventilation of the room. Excessively high $CO_2$ concentration is associated with poor indoor environment, and 1000 ppm has been accepted as a hygienic upper limit by, among others, the American Society of Heating, Refrigeration and Air-Conditioning Engineers (ASHORE). $CO_2$ is thus used as a tracer gas or indicator of air quality. The concentration in ppm constitutes a quantitative measure which can be used for monitoring and control of indoor air quality. A kindred application area for $CO_2$ sensors is personal presence detection, as a part of security systems. At fires the $CO_2$ concentration increases rapidly already at the initial stage, which can be correspondingly put to use. Also worth mentioning are a number of medical applications. $CO_2$ sensors can be used for respiratory patient monitoring, for evaluation of lung function, and respirator therapy control.

Instruments and transducers for the measurement of $CO_2$ concentration in air have been described in the patent literature, and also in the form of commercially available products on the market. The majority of these are based on the absorption specter within the infrared wavelength area of electromagnetic radiation of the $CO_2$ molecule. Such specters can be detected and analyzed by spectroscopic instruments according to known technology. By measuring at specific wavelengths where the absorption of $CO_2$ deviates from other constituents of air, it is possible to extract an output signal with required sensitivity and specificity. One problem with this measuring principle is, however, contamination by dust, liquid drops, smoke particles etc, which put specific demands either on the design or on short maintenance intervals, in addition to high demands on mechanical precision. As a consequence, these instruments have a high production cost, but still limited reliability. They are therefore being put use only to a limited extent within the indicated application areas.

SUMMARY OF THE INVENTION

These and related problems are solved by the present invention. It is based on indirect measurement or the average molecular mass, the variation of which under certain circumstances is assumed to be dominated by variations of the $CO_2$ concentration, by measuring the velocity of sound which is approximately given by $$c=\sqrt{(RT\gamma/M)} \quad (1)$$

where c is the velocity of sound, R the general gas constant= 8.314 J/mol K, T the absolute temperature, γ the ratio of specific heat at constant pressure and volume, respectively, and M is the average molecular mass. The relation assumes that the gas mixture, air in this case, can be considered an ideal gas according to well known physical principles.

Equation (1) has been utilized in transducers and instruments for the determination of concentration ratios in binary gas mixtures, i.e., mixtures with two components having differing molecular mass. If the temperature is held constant, the concentration ratio between the two components can be determined by measuring the sound velocity and using equation (1).

The present invention is based on the fact that that the molecular mass of $CO_2$ ($M_{CO}$=44 atomic units) is considerably higher than the average value of air ($M_{air}$=28.9). At increased $CO_2$ concentration the average air value will increase, resulting in a decreasing value of the sound velocity. Corresponding changes are obtained for any additional species having dissimilar molecular mass. For example, an increasing concentration of water vapor, $H_2O$ ($M_{H2O}$=18), will get rise to a net decrease of the average molecular mass, in other words, a signal with opposite sign. The equation below specifies the relation between small variations in temperature, and the concentration of carbon dioxide, $X_{CO2}$, and water vapor, $X_{H2O}$, and their influence on the velocity of sound (the variations of the variables are denoted Δ):

$$\Delta c/c_o = \Delta T/2T_o - (M_{CO2}-M_{air})/2M_{air} * X_{CO2} + (M_{air}-M_{H2O})/2M_{air} * XH20 \quad (2)$$

Equation (2) illustrates the existence of both desired and undesired functional relations. An observed variation of the sound velocity is not necessarily caused by a variation of the carbon dioxide concentration but may be due to a variation in temperature or humidity. From equation (2) it is also clear that these undesired relations have a character of an offset shift, i.e., within the linear approximation, the offset level of the output signal is influenced. According to this approximation, however, the influence on the calibration factor, i.e., the multiplicative factor in front of $X_{CO2}$, is negligible.

In the present invention, automatic correction of eventual, undesired variations of the offset level is provided, irrespective of them being caused by variations in temperature, humidity, or something else. The basis for this automatism is partly the assumption that prevailing undesired offset variations are considerably slower than the processes one wishes to measure, and partly that the sensor signal lapse in time includes instants when a true signal output value can be securely assumed. Such an assumption is realistic in applications which do not require absolute readings, but when it is sufficient to relate the output signal, e.g., to the background level of fresh air, as mentioned above. If the sensor from time to time is exposed to fresh air, the measuring value at this point will be represented by an extreme value, since the $CO_2$ concentration will hardly ever fall below the background level of fresh air. Exactly these conditions prevail in the application areas mentioned above. In empty, ventilated localities, the $CO_2$ concentration will return to the fresh air level, and the appearing signal level will represent an extreme level which may be the basis of automatic offset correction. The corresponding condition is also valid in the medical applications, although the time scale in this case is considerably shorter. In other applications, the average signal value may be used as offset reference. More generally speaking, it could be stated the statistically calculated parameters based on accumulated measuring values during a certain time will be the basis of the offset correction.

The requirement mentioned above that undesired offset variations should be slow can be met by appropriate design of the sensor according to the invention. Temperature variations within an air-filled measuring cell could be made slow by designing the measuring cell like a thermos flask, i.e., with an inner and outer shield separated by thermally isolating material. Additional thermal stabilization can be obtained by active thermosetting of the inner shield according to known technology. Variations of humidity can be made slow by ensuring that the air flow being measured first will pass a material with high porosity and high surface density of polar molecular groups. To such material, other polar molecules, such as water molecules, will be adsorbed, which makes the humidity of a passing air flow being leveled in time, as desired.

BRIEF DESCRIPTION OF THE DRAWINGS

The sensor according to the invention will be described in more detail below, in relation to the enclosed drawing, FIG. 1, which schematically depicts the design of the sensor, and its function, in the form of a block diagram.

DETAILED DESCRIPTION OF THE DRAWINGS

Figure 1:
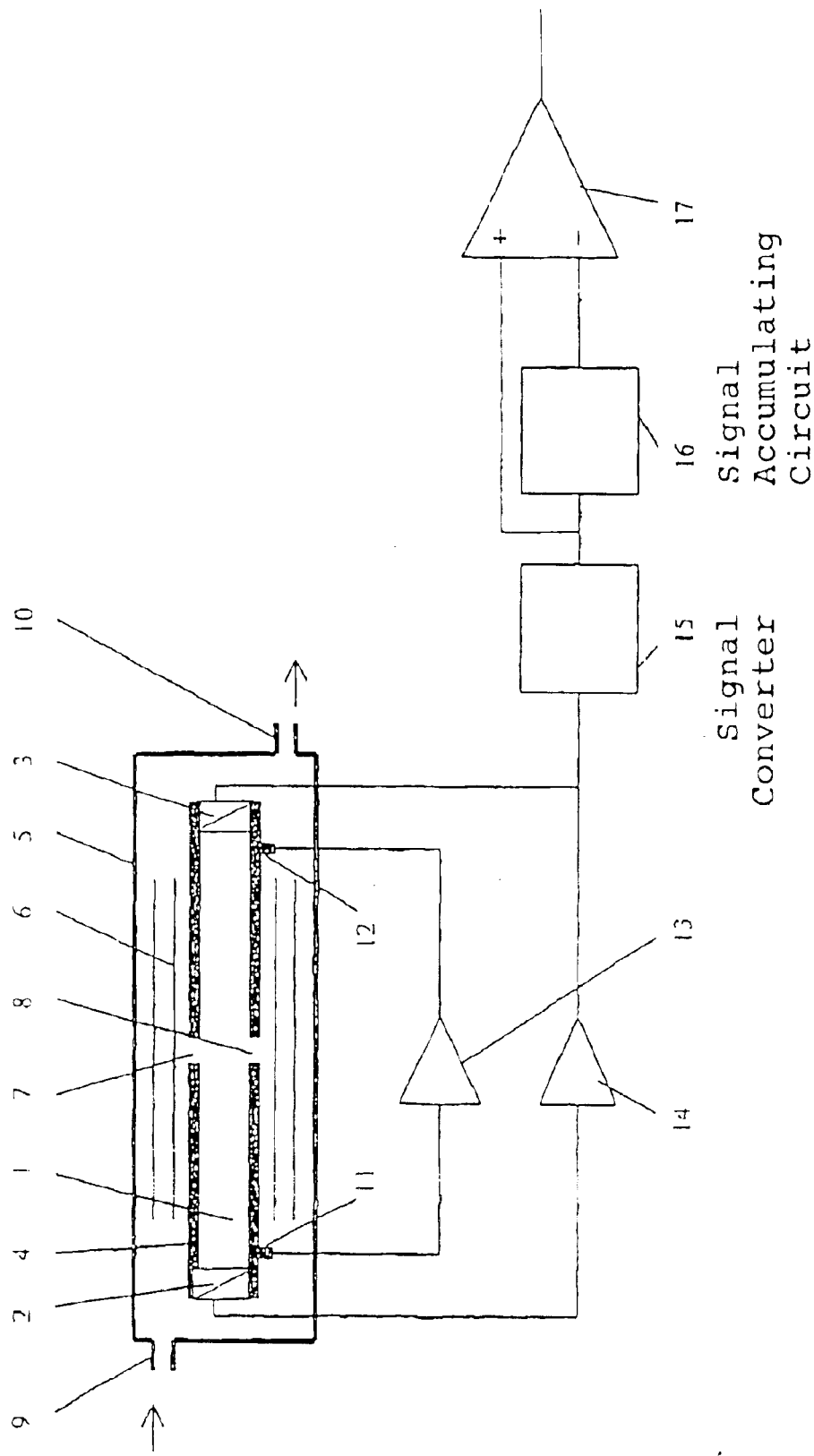

The present invention relates to a sensor for the measurement of carbon dioxide within a flow of air being input to at least one measuring cell (1) connected to at least one electroacoustic element (2,3) for transmitting and receiving airborne acoustic waves within said measuring cell (1) characterized in that at least one measuring signal is generated and being a monotonous function of the propagation velocity of said waves, and an indirect measure of said carbon dioxide concentration, said sensor including at least one automatic offset correction functionality for compensation of undesired offset variation of said measuring signal. Specifically, the offset correction functionality is advantageously based on the measurement or calculation of the average measuring signal, extreme value or other statistical parameters during a certain period of time, being shorter than the lapse of offset variations.

The sensor according to the invention includes a cylindrical measuring cell or chamber 1, shown schematically as a longitudinal section in FIG. 1. Within the measuring cell 1, continuous or intermittent measurements of the velocity of sound is being performed. A flow of air is ensuring adequate exchange of air between the actual measuring position, and the measuring cell. This air flow may be effected by diffusion, convection, a pressure gradient, or any other passive or active drive mechanism by which the air flow may be controlled with respect to its magnitude. The measurement itself is effected by emission of airborne acoustic waves within the measuring cell 1, and by measuring their propagation velocity.

The measuring cell 1 is demarcated by two electroacoustic elements 2, 3 and an inner cylindrical sheath 4. The electrostatic elements can e.g., consist of thin plates of a piezoelectric material, e.g., lead zircon ate-titanates, with metal depositions. According to known principles, an electric field within the material will give rise to a mechanical strain, which will be coupling to airborne acoustic waves. In this way, an electroacoustic element will act as transmitter of acoustic waves. Preferably, the.geometry of the piezoelectric plate is designed so that the frequency of a mechanical resonance oscillation coincides with the desired acoustic emission frequency. In the present invention, it is advantageous to operate in the ultrasonic frequency range, i.e., above the audible range. Electroacoustic elements operating in frequencies from 30 kHz to 1 MHz are commercially available. Since the piezoelectric effect is reversible, the same type of electroacoustic element used both as transmitters and receivers. One is not limited by piezoelectric transmitters/receivers either. Electrostatic/capacitive drive/detection can also be used, as well as magnetostrictive transducers.

In a preferred embodiment, Continuous acoustic waves having approximately constant amplitude are transmitted from the electroacoustic transmitter 3 and received by the electroacoustic receiver 2. The elements 2 and 3 are frequency determining elements in a free running oscillator, the frequency of which is also influenced by velocity of propagation of the airborne acoustic waves within the chamber 1. The elements 2 and 3 are connected to an electronic amplifier 14 which according to known technology includes the require active and passive circuit elements for this oscillator function. The oscillation frequency is influenced by the transit time for the acoustic waves between the elements 3 and 2, and since the distance is constant, it will be univocally dependent on the sound velocity.

In an alternative embodiment, short pulses will be emitted instead of continuous waves, followed by measurement of the time for their propagation through the medium. The advantage of this alternative is that only one electroacoustic element directed towards a sound reflecting wall is required, according to the well known pulse echo principle. The disadvantage is a more complicated detection procedure.

The inner sheath 4 of the measuring cell is preferably fabricated in a metallic material with good thermal conductivity, e.g., copper or aluminium. Typical dimensions are inner diameter 3–10 mm, length 3–15 mm, the active length being preferably a multiple of half the wavelength of sound at the operating frequency. The sheath 4 is provided with openings 7, 8 which allow connection between the inner chamber and its ambient. The connection allows passage of gas by diffusion, convection or pressure driven flow. Normally, the.g., as exchange between the inner volume of the chamber 1 and its ambient is effected passively without power supply dedicated for the purpose. By adjacent positions of the openings 7, 8 as drawn in FIG. 1, the major gas flow direction will be perpendicular to the propagation direction of the acoustic waves between the elements 3 and 2. A strong flow in the direction of propagation of the acoustic waves would have resulted in a measuring error due to the interdependence between the sound velocity and flow velocity.

The sensor may also be characterized by at least one opening (7,8) to the inner of said measuring cell (1) positioned so that said air flow direction with said measuring cell (1) is essentially perpendicular to the propagation direction of said acoustic waves, and that the attenuation of said acoustic waves between said measuring cell and the ambient exceeds 60 dB.

At least one temperature sensor 11, e.g., a thermistor, and one or several resistive heating elements 12 are attached to the sheath 4, with good thermal contact to its surface. The thermistor 11 and the heating element are connected to an electronic control circuit 13, which according to known principles generates a current through the heating elements 12 whereby carefully controlled heating is effected of the sheath 4 and the air volume contained in the measuring cell 1. With the described devices it is possible to maintain the temperature of the measuring cell with an accuracy of 0.01° C., or better. A suitable temperature value is immediately above the operating temperature range of the sensor, e.g., 40° C.

The inner sheath is surrounded by a porous material 6 with high surface density of polar molecular groups. The purpose of this material is, as described earlier, to bring about a levelling effect on prevailing variations of humidity of incoming air, before it reaches the measuring cell 1. An example of a suitable material is cellulose, which has the ability to bind several mass percent of water. Paper and cotton consist mainly of cellulose, and therefore it is easy to accomplish adequate material forms, such as sheets, bands, threads, oriented so that the air flow will pass alongside its surfaces. The porous structure of the material 6 is also appropriate, since it leads to good thermal isolation to the ambient, which is important for the temperature control mentioned above.

The measuring cell 1, the inner sheath 4, and the material 6 are further surrounded by an outer sheath 5 with openings 9, 10, the size of which is determining the magnitude of the air flow to and from the measuring cell 1. The degree of levelling of humidity within the measuring cell 1 compared to variations of input air flow is determined, not only by the mass of the material 6 and its water adsorbing capacity, but also by the magnitude of the air flow and its distribution over the surface of the material 6. For each type of measuring situation, these factors may be dimensioned to provide the desired degree of levelling.

The signal from the free running oscillator formed by the electroacoustic elements 2, 3 and the amplifier 14 has, as described earlier, the form of an alternating voltage, the frequency variations of which constitutes a monotonous function of the sound velocity, and an indirect measure of the carbon dioxide concentration within the cell 1, but is also including the undesired variations as described above. This signal is input to a signal converter 15 which in its simplest embodiment is a frequency/voltage converter according to known technology. The output of the signal converter 15 is thus a measuring signal in the form of a dc voltage, exhibiting variations corresponding to the frequency variations mentioned above. Further is an offset correcting unit which in its simplest embodiment consists of an signal accumulating circuit 16, and a differential amplifier 17. The signal accumulating circuit stores the measuring signal during a certain period of time, and outputs an accumulated value corresponding to the average value of the measured signal, or one or several extreme values, or other statistically calculated parameters. The technique to carry out such computing operations with operational amplifiers and passive circuit elements is well known in the literature. The output signal after the differential amplifier 17 consists of the difference between the actual measuring signal, and this accumulated value. Assuming that the signal average or some extreme value can be related to a certain carbon dioxide concentration, e.g., the fresh air background level as described above, the function as described above constitutes an automatic offset correction of the output signal.

Alternatively, the signal processing operations described above can, of course, be performed in digital from, rather than on an analog dc voltage. This can be advantageous, especially when the functionality of offset correction demands more complex statistical computations. The simplest form of automatic offset correction consists of a passive high pass filter, which is known to be realisable with a resistor R and a capacitor C. The period of time involved in the correction is determined by the filter time constant RC, which with practically reasonable component values may amount to a few minutes. If longer periods are desired, digital solutions are more appropriate.

The sensor according to the invention can be varied in a multitude of manners within the scope of the claims mentioned below.

What is claimed is:

1. A sensor for the measurement of carbon dioxide within a flow of air being input to at least one measuring cell (1) connected to at least one electroacoustic element (2,3) for transmitting and receiving airborne acoustic waves within said measuring cell (1) characterised in that at least one measuring signal is generated and being a monotonous function of the propagation velocity of said waves, and an indirect measure of said carbon dioxide concentration, said sensor including at least one automatic offset correction functionality for compensation of undesired offset variations of said measuring signal and wherein said offset correction functionality is based on the measurement or calculation of the average measuring signal, or extreme values calculated during a period of time, being shorter than the time lapses of said undesired offset variations.

2. The sensor according to claim 1 characterised by at least one accumulating, filtering, or time delaying functionality for minimising the influence of said offset variations.

3. The sensor according to claim 1 characterised in that said air flow is effected by diffusion, convection, or a pressure gradient being actively or passively controllable in magnitude.

4. The sensor according to claim 1 characterised in that said air flow before it reaches said measuring cell (1) is passing material with high porosity and surface density of polar molecular groups, said material has the form of thin sheets, bands, or threads being oriented so that said air flow will pass alongside the surfaces of said sheets, bands, or threads.

5. The sensor according to claim 1 characterised in that said measuring cell (1) is surrounded by at least one inner volume and one outer sheath (4, 5) whereby at least one temperature sensor (11) and at least one resistive heating element (12) has good thermal contact with said inner sheath, that said outer sheath (5) is thermally isolated from said inner sheath (4), and that the output signal of said temperature sensor (11) via at least one control circuit (13) is being utilized for control of power dissipation of said heating element (12).

6. The sensor according to claim 1 characterised by at least one opening (7, 8) to the inner volume of said measuring cell (I) positioned so that said air flow direction within said measuring cell (1) is essentially perpendicular to the propagation direction of said acoustic waves, and that the attenuation of said acoustic waves between said measuring cell and the ambient exceeds 60 dB.

7. The sensor according to claim 1, characterised by at least one amplifier element (14) connected to said at least one electroacoustic element (2,3), forming a free running oscillator, the frequency of which is a monotonous function of the velocity of sound in said measuring cell (1).

8. The sensor according to claim 1 characterised by at least one signal processing functionality (15,17).

9. A sensor for the measurement of carbon dioxide within a flow of air being input to at least one measuring cell (1) connected to at least one electroacoustic element (2,3) for transmitting and receiving airborne acoustic waves within said measuring cell (1) characterised in that at least one measuring signal is generated and being a monotonous function of the propagation velocity of said waves, and an indirect measure of said carbon dioxide concentration, said sensor including at least one offset correcting unit for compensation of undesired offset variations of said measuring signal, and wherein said offset correction correcting unit comprises a signal accumulating circuit (16), and a differential amplifier (17).

* * * * *